US005657364A

United States Patent [19]
Pfoh

[11] Patent Number: 5,657,364
[45] Date of Patent: Aug. 12, 1997

[54] METHODS AND APPARATUS FOR DETECTING BEAM MOTION IN COMPUTED TOMOGRAPHY IMAGING SYSTEMS

[75] Inventor: Armin Horst Pfoh, Niskayuna, N.Y.

[73] Assignee: General Electric Company, Milwaukee, Wis.

[21] Appl. No.: 572,574

[22] Filed: Dec. 14, 1995

[51] Int. Cl.⁶ .................................... H01J 35/30
[52] U.S. Cl. .................. 378/137; 378/145; 378/4
[58] Field of Search .................... 378/145, 146, 378/147, 149, 150, 151, 154, 155, 4, 19, 137

[56] References Cited

U.S. PATENT DOCUMENTS

| | | | |
|---|---|---|---|
| 4,675,892 | 6/1987 | Plessis et al. | 378/126 |
| 4,812,983 | 3/1989 | Gullberg et al. | 378/901 |
| 4,991,189 | 2/1991 | Boomgaarden et al. | 378/4 |
| 5,131,021 | 7/1992 | Gard et al. | 378/8 |

*Primary Examiner*—Don Wong
*Attorney, Agent, or Firm*—John S. Beulick; John H. Pilarski

[57] ABSTRACT

An attenuator and detector cell arrangement for generating a signal ratio representative of focal spot position is described. The ratio is highly sensitive to focal spot position and facilitates generating, or reconstructing, a high quality image from the projection data. Further, and importantly, even if one detector cell is fully flooded, the signal intensity from such cell will vary depending upon the alignment between the focal spot and attenuator slot. Therefore, the focal spot movement detector is effective for detecting fan beam movement even if the detector cell is fully flooded. In one embodiment, the x-ray beam attenuator is configured to be positioned over the detecting surface of z-position detection cells. Slots or openings extend through the attenuator so that at least a portion of each detector cell is in free communication with an x-ray beam from the x-ray source. The slots are positioned and oriented so that one detector cell signal has its highest x-ray response at one extreme position along the focal spot trajectory and the other detector cell has its highest x-ray response at the other extreme position along the focal spot trajectory.

16 Claims, 3 Drawing Sheets

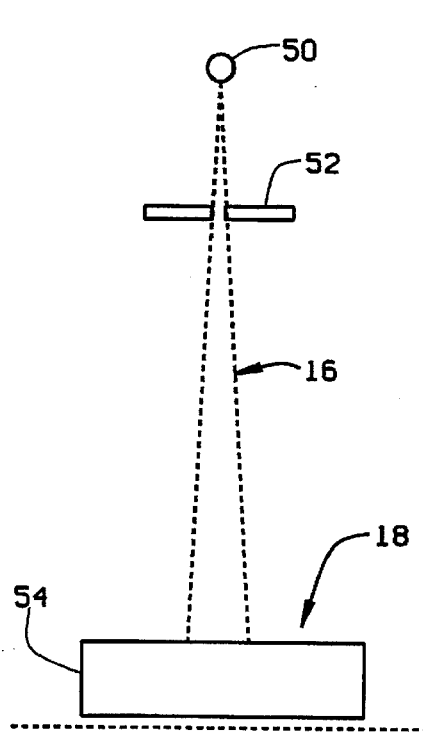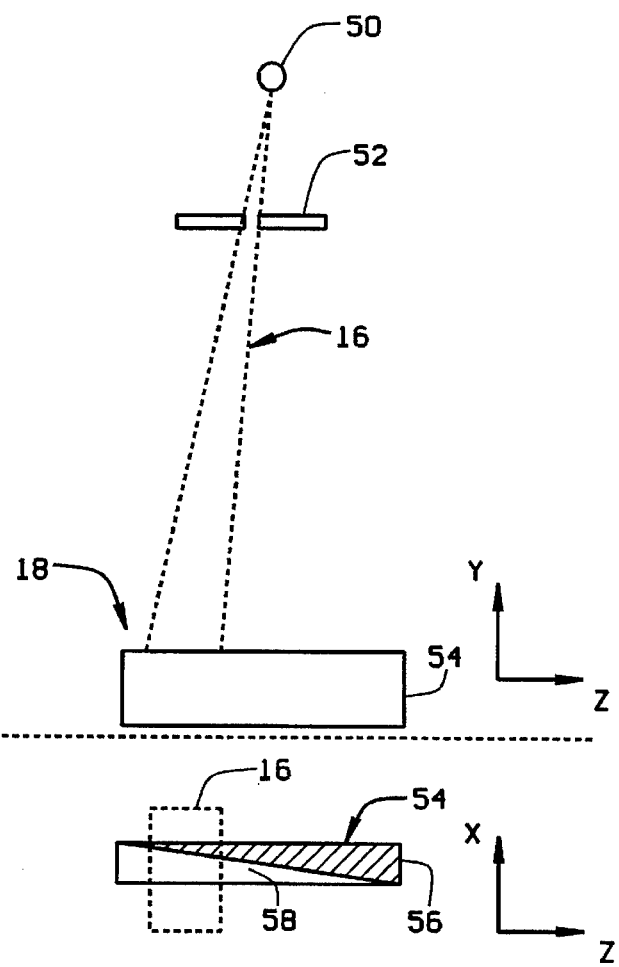
FIG. 3a (PRIOR ART)
FIG. 3b (PRIOR ART)

5,657,364

METHODS AND APPARATUS FOR DETECTING BEAM MOTION IN COMPUTED TOMOGRAPHY IMAGING SYSTEMS

FIELD OF THE INVENTION

This invention relates generally to computed tomography (CT) imaging and more particularly, to detecting x-ray beam motion while performing a scan with a CT system.

BACKGROUND OF THE INVENTION

In at least one known CT system configuration, an x-ray source projects a fan-shaped beam which is collimated by a pre-patient collimator to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To generate a high quality image, the x-ray source position during a CT scan is required to be known with a very high precision. In at least one known CT system, gravitational and thermal effects cause focal spot motion, i.e., motion of the x-ray source in the z-axis relative to the detector and pre-patient collimator. One component of the focal spot motion causes the fan beam to move along the z-axis. Specifically, focal spot motion displaces the fan beam at the detector location according to the ratio of collimator to detector distance and collimator to focal spot distance. This ratio is typically larger than one. The fan beam movement, or displacement, if uncorrected, results in image artifacts and otherwise degrades image quality.

In known CT systems, dedicated detectors with z-resolution, e.g., z-wedge detectors, are used to detect displacement of the fan beam along the z-axis. Such detectors are outside the fan beam area that is introduced to the object to be scanned. As a result, such detectors are always exposed to the unattenuated beam. Z-wedge detectors require that the detector z-dimension be larger than the fan beam z-dimension. Any fan beam movement in the z-direction then affects the intensity of the signal output by the detector. By monitoring the signal intensity at the z-wedge detector, fan beam motion, and thus focal spot motion, can be detected.

However, known z-wedge detectors and other known position sensitive structures are ineffectual if the entire surface area of the detectors is flooded by the fan beam. Particularly, if the fan beam floods the entire z-wedge detector cell, even during z-axis displacement, the z-wedge detector cell output signal remains constant. Under such conditions, a z-wedge detector is unable to determine focal spot motion.

It is desirable to detect fan beam movement with high accuracy so that a high quality image with a low level of artifacts can be generated. It also is desirable to detect such fan beam movement even if the fan beam floods the entire detector cell surface.

SUMMARY OF THE INVENTION

These and other objects may be attained in a system which, in one embodiment, is implemented in a multi-slice CT imaging system and monitors linear focal spot motion in the z-axis by determining signal intensity at two detector cells that are aligned in the imaging plane but displaced along the z-axis. Particularly, an x-ray beam attenuator is positioned over the detecting surface of z-position detection cells. Slots or openings extend through the attenuator so that at least a portion of each detector cell is in free communication with an x-ray beam from the x-ray source. As one specific example, two adjacent detector cells in separate detector cell rows are used to detect fan beam motion. An attenuator having a slot therethrough is positioned on each detector cell. The slots are positioned so that one detector cell signal has its highest x-ray response at one extreme position along the focal spot trajectory.

In operation, when the focal spot is in its desired, centered position, the subject detector cells generate signals of about the same magnitude. The signal ratio for such cells therefore is about one.

If the focal spot, and thus the fan beam, moves with respect to the z-axis, the signal intensity from one cell will increase and the signal intensity from the other cell will decrease. Therefore, depending upon the direction of focal spot movement with respect to the z-axis, the detector cell signal ratio will increase to a value greater than one or decrease to a value less than one.

The signal ratio can then be used during image reconstruction to correct the projection data acquired from the detector arrays. Since the attenuator structure described above is highly sensitive to focal spot movement, such attenuator facilitates generating, or reconstructing, a high quality image from the projection data. Further, and importantly, even if one detector cell is fully flooded, the signal intensity from such cell will vary depending upon the alignment between the focal spot and attenuator slot. Therefore, the above described focal spot movement detector is effective for detecting fan beam movement even if the detector cell is fully flooded.

BRIEF DESCRIPTION OF THE DRAWINGS

FIGS. 3a and 3b are schematic diagrams of a known z-wedge detector under various operating conditions.

DETAILED DESCRIPTION OF THE DRAWINGS

Figure 1:
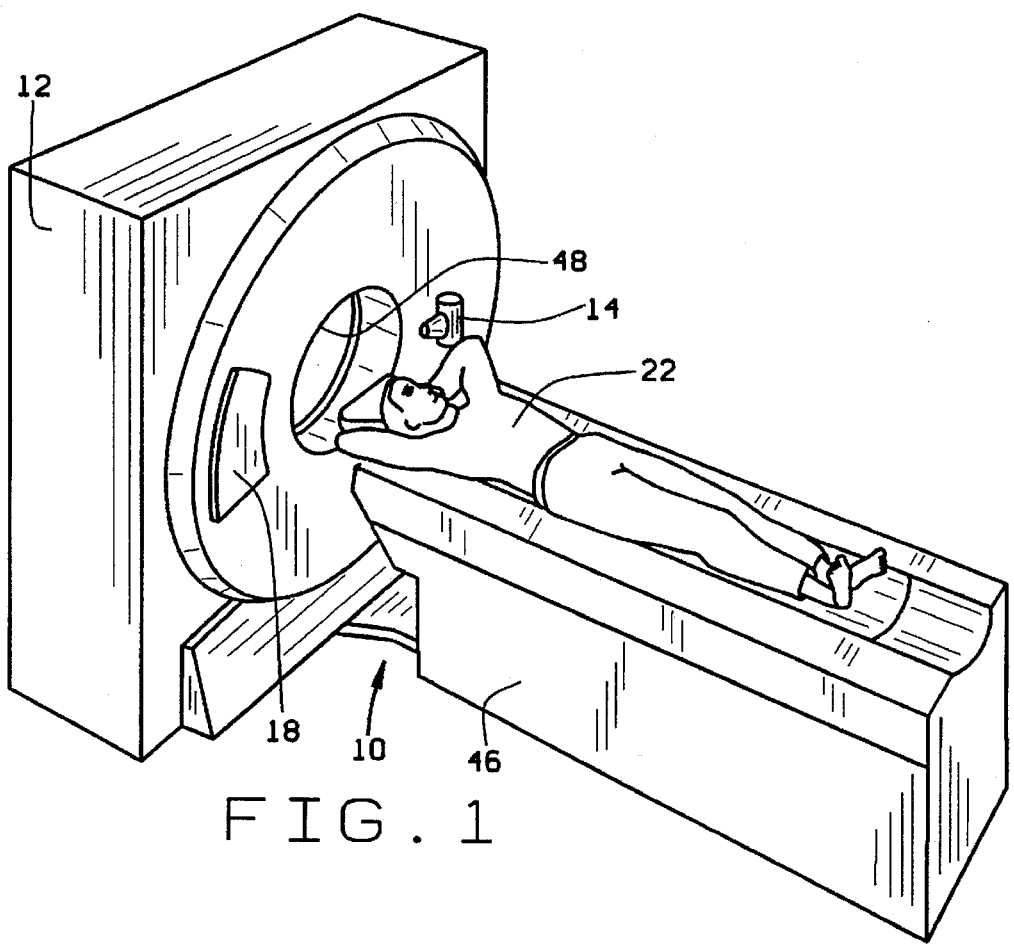
FIG. 1 is a pictorial view of a CT imaging system.
Figure 2:
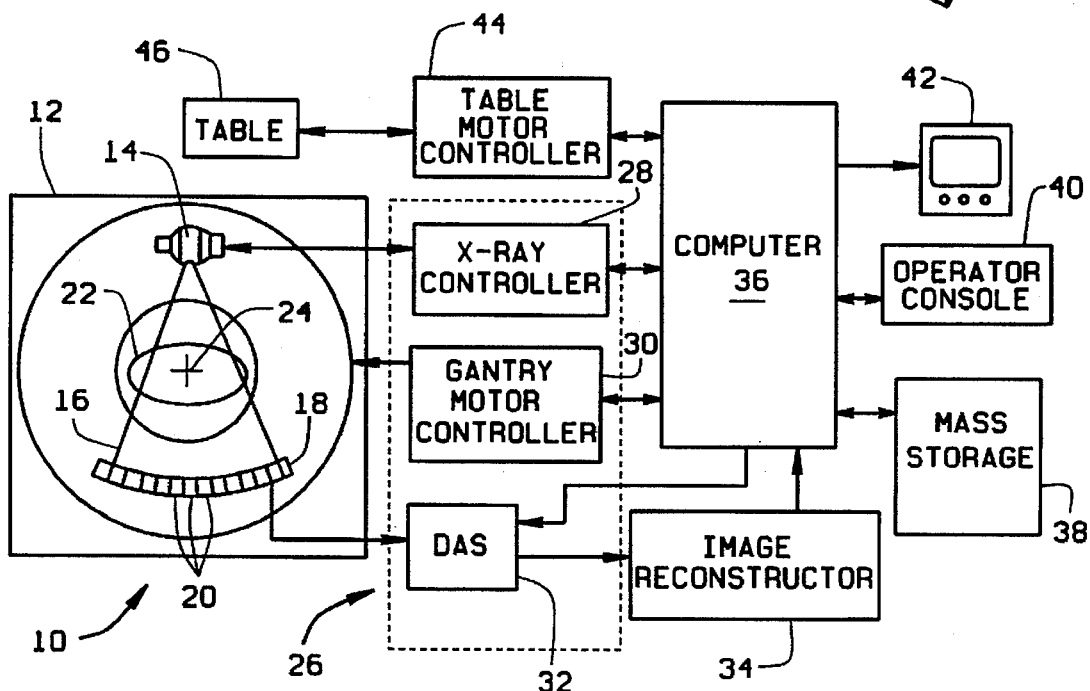
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Referring to FIG. 3a, and with respect to known fan beam movement detection, x-ray source 14 (FIG. 2) has a focal spot 50 from which x-ray beam 16 emanates, and x-ray beam 16 is collimated by collimator 52 and is projected toward detector array 18. Fan beam 16 impinges on the face of detector array 18 (FIG. 2), including on the face of z-axis offset detector element 54. The face of z-axis offset detector 54 is partially occluded by a wedge filter 56 which is tapered to block a changing percentage of active x-ray sensitive surface 58 of detector 54 as a function of the fan beam position with respect to the z-axis. As previously described, the focal spot 50 may not be aligned with the collimator 52 in the z-axis either because of thermal drift, gravitational drift, or because of minor misalignment of x-ray source 14 (FIG. 1) during assembly.

As shown in FIG. 3a, beam 16 and focal spot 50 are substantially aligned with detector 54 and a portion of beam 16 falls on the center of the face of detector 54. Under such conditions, the intensity of the signal generated by cell 54 has a first magnitude.

Referring to FIG. 3b, focal spot 50 is shown displaced in the z-axis direction. The effect of this misalignment is to displace fan beam 16 in the z-axis. At detector 54, fan beam 16 may move significantly due to minor focal spot 50 movement. Under such conditions, a greater area of active surface 58 of detector cell 54 receives x-ray beam 16. Therefore, the intensity of the signal generated by cell 54 has a second magnitude, which is greater than the first magnitude.

The signal intensity output by z-axis offset detector 54 changes as fan beam 16 moves in the z-axis direction. Such changes can be used to determine movement of focal spot 50. A detailed description of the detection of fan beam position, through the use of a wedge filter in conjunction with a z-axis offset detector, is described in U.S. Pat. No. 4,559,639, entitled "X-ray Detector with Compensation for Height-Dependant Sensitivity and Method of Using Same", issued on Dec. 17, 1985 and assigned to the present assignee If z-axis offset detector 54 is continuously fully flooded by fan beam 16, however, the intensity of the signal received at detector 60 will not change, even if fan beam 16 moves with respect to the z-axis. Therefore, the known z-axis offset detector 54 is not reliable when fan beam 16 z-dimension is continuously larger than detector 54 z-dimension, i.e., detector 54 is "flooded".

Figure 4:
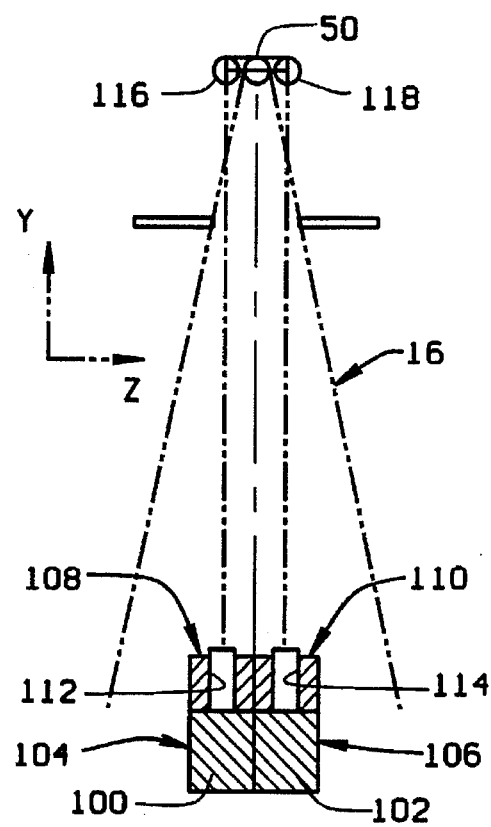
FIG. 4 is a schematic diagram of an attenuator in accordance with one embodiment of the present invention.

One embodiment of the present invention is illustrated in FIG. 4. More specifically, in one embodiment, two adjacent detector cells 100 and 102 in separate detector cell rows 104 and 106 are aligned in the imaging plane but are displaced along the z-axis. X-ray attenuators 108 and 110 are placed over respective cells 100 and 102. Slots 112 and 114 extend through attenuators 108 and 110, respectively, so that only a portion of each detector cell 100 and 102 is in free communication with x-ray beam 16. Slots 112 and 114 are positioned so that each slot 112 and 114 aligns with an extreme position 116 and 118 of focal spot 50. Specifically, positions 116 and 118 represent the maximum movement of focal spot 50 in the z-axis direction.

In operation, when focal spot 50 is in its desired, centered position, detector cells 100 and 102 generate signals of about the same magnitude. The signal ratio for signals output by such cells 100 and 102 therefore is about one.

If focal spot 50 moves to position 116, for example, the signal intensity from cell 100 increases and the signal intensity from cell 102 decreases. Therefore, depending upon the direction of focal spot movement with respect to the z-axis, the detector cell signal ratio will increase to a value greater than one or decrease to a value less than one. A similar result is obtained if focal spot 50 moves to position 118, with the exception that the signal intensity from cell 102 increases and the signal intensity from cell 100 decreases.

The signal ratio is used, by computer 36 (FIG. 2), during image reconstruction to determine the actual focal spot position and to correct the projection data acquired from the detector arrays. Since the signal ratio described above is highly sensitive to focal spot movement, such ratio facilitates generating, or reconstructing, a high quality image from the projection data. Further, and importantly, even if detector cell 100, 102 is fully flooded, the signal intensity from such cell 100,102 will vary depending upon the alignment between focal spot 50 and attenuator slot 112,114. Therefore, the signal ratio is effective for determining focal spot movement even if detector cell 100,102 is fully flooded at all times.

Figure 5:
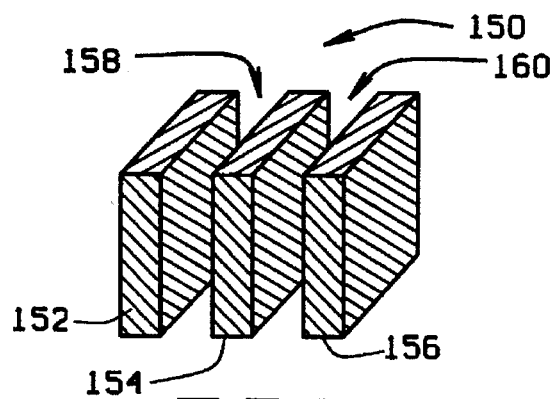
FIG. 5 is a perspective view of an attenuator in accordance with one embodiment of the present invention.

FIG. 5 is a perspective view of an attenuator 150 in accordance with one embodiment of the present invention. Attenuator 150 includes a plurality of spaced, adjacent rectangular blocks 152, 154 and 156 constructed from x-ray absorbing material. Slots 158 and 160 between adjacent blocks 152,154 and 154,156 are x-ray beam paths through which x-rays may pass to a detector cell. Slots 158 and 160, in operation, would be aligned with respective extreme positions of the x-ray source focal spot.

Figure 6:
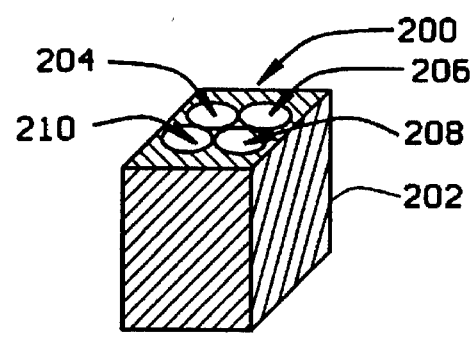
FIG. 6 is a perspective view of an attenuator in accordance with another embodiment of the present invention.

FIG. 6 is a perspective view of an attenuator 200 in accordance with another embodiment of the present invention. Attenuator 200 includes a block 202 of x-ray absorbing material. Cylindrical openings 204, 206, 208 and 210 extend through block 202 and form x-ray beam paths through which x-rays may pass to a detector cell. Openings 204,210 and 206,208, in operation, would be aligned with respective extreme positions of the x-ray source focal spot.

With respect to both attenuators 150 and 200, a signal ratio can be generated from outputs of the associated detector cells. Such signal ratio is highly sensitive to focal spot movement and can be used to determine the actual focal spot position and reconstruct a high quality image from the projection data. Further, and importantly, even if an associated detector cell is fully flooded, the signal intensity from such cell will vary depending upon the alignment between the focal spot and the orientation of the attenuator slot or opening. Therefore, the signal ratio is effective for determining focal spot movement even if the detector cell is fully flooded.

Of course, the shape of the attenuator openings or slots does not necessarily have to be cylindrical, as shown in FIG. 6 as openings 204, 206, 208 and 210, or substantially rectangular, as shown in FIG. 5 as slots 158 and 160. Such slots or openings could have many other shapes such as triangular.

Further, although the above described embodiments include two openings or slots aligned with respective extreme positions of the x-ray source focal spot, it is contemplated that one attenuator with an opening or slot could be placed over one detector with the opening or slot aligned with one respective extreme position of the x-ray source focal spot. When the x-ray focal spot is in the one extreme position, the detector output would be at its highest level. When the x-ray focal spot is in the other extreme position, the detector output would be at its lowest level.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, the detector displacement does not necessarily have to be along the same orientation as the linear motion to be monitored i.e., along the z-axis. For example, two adjacent detectors along the x-axis could be aligned so that each detectors intensity is related to focal spot z-axis displacement. Moreover, while the above description was in terms of a multi-slice detector array, many other arrays can be used. Accordingly, the spirit and scope of the invention are to be limited only by the terms of the appended claims.

What is claimed is:

1. A method for determining focal spot movement in a computed tomography system, the computed tomography system including an x-ray source for producing an x-ray fan beam along an imaging plane and at least first and second detector cells, the detector cells configured for receiving x-rays of the fan beam, an attenuator positioned over the two cells, the attenuator defining x-ray beam passages therethrough so that the signal output by the first detector is at a maximum intensity when the x-ray source focal spot is aligned therewith and so that the signal output by the second detector is at a maximum intensity when the x-ray source focal spot is aligned therewith, said method comprising the steps of:

sampling the detector cell output signals from the first and second detector cells during a scan;

generating a ratio of the sampled output signals representative of the intensity of one output signal as compared to the intensity of the other output signal; and using the generated ratio to calibrate the projection data collected during the scan.

2. A method in accordance with claim 1 wherein a first x-ray beam passage aligns with a first extreme position of the x-ray source focal spot and a second x-ray beam passage aligns with a second extreme position of the x-ray source focal spot.

3. A method in accordance with claim 2 wherein the first detector cell receives x-rays via the first x-ray beam passage and the second detector cell receives x-rays via the second x-ray beam passage.

4. A method in accordance with claim 3 wherein the intensity of the signal output by the first detector cell is at a maximum when the x-ray source focal spot is aligned with the first x-ray beam passage and the signal output by the second detector cell is at a maximum when the x-ray source focal spot is aligned with the second x-ray beam passage.

5. An x-ray beam position detection apparatus for determining focal spot movement in a computed tomography system, the computed tomography system including an x-ray source for producing an x-ray fan beam along an imaging plane, said apparatus comprising:

a first x-ray detector cell;

a second x-ray detector cell displaced from said first x-ray detector cell in a z-axis;

a first attenuator positioned over said first cell, said first attenuator defining a first x-ray beam passage therethrough so that a signal output by said first detector is at a maximum intensity when the x-ray source focal spot is aligned with said first passage;

a second attenuator positioned over said second cell, said second attenuator defining a second x-ray beam passage therethrough so that a signal output by said second detector is at a maximum intensity when the x-ray source focal spot is aligned with said second passage; and a computer coupled to the outputs of said first and second cells, said computer programmed to:
sample the output signals of said first and second detector cells during a scan; and
generate a ratio of the sampled output signals representative of the intensity of one output signal as compared to the intensity of the other output signal.

6. Apparatus in accordance with claim 5 said first x-ray beam passage aligns with a first extreme position of the x-ray source focal spot.

7. Apparatus in accordance with claim 5 wherein said first attenuator comprises a block having cylindrical openings extending therethrough, said cylindrical openings forming said x-ray beam passages.

8. Apparatus in accordance with claim 5 said first x-ray beam passage aligns with a first extreme position of the x-ray source focal spot and said second x-ray beam passage aligns with a second extreme position of the x-ray source focal spot.

9. Apparatus in accordance with claim 8 wherein the intensity of the signal output by said first detector cell is at a maximum when the x-ray source focal spot is aligned with said first x-ray beam passage and the signal output by said second detector cell is at a maximum when the x-ray source focal spot is aligned with said second x-ray beam passage.

10. Apparatus in accordance with claim 5 wherein said first attenuator comprises a plurality of spaced, adjacent rectangular blocks.

11. Apparatus in accordance with claim 10 wherein said blocks are constructed from x-ray absorbing material and slots are established between adjacent blocks to form said x-ray beam passages.

12. In a computed tomography imaging system including an x-ray source for producing an x-ray fan beam along an imaging plane, an x-ray beam position detection apparatus for determining x-ray beam focal spot movement, said beam position detection apparatus comprising:

first and second x-ray detector cells, said first cell being displaced from said second cell in a z-axis;

an attenuator positioned over said first and second cells, said attenuator defining first and second x-ray beam passages therethrough so that a signal output by said first detector is at a maximum intensity when the x-ray source focal spot is aligned with said first passage and so that a signal output by said second signal is at a maximum intensity when the x-ray source focal spot is aligned with said second passage; and a processor coupled to the outputs of said first and second cells, said processor programmed to:
sample the output signals of said first and second detector cells during a scan; and
generate a ratio of the sampled output signals representative of the intensity of one output signal as compared to the intensity of the other output signal.

13. Apparatus in accordance with claim 12 said first x-ray beam passage aligns with a first extreme position of the x-ray source focal spot and said second x-ray beam passage aligns with a second extreme position of the x-ray source focal spot.

14. Apparatus in accordance with claim 13 wherein the intensity of the signal output by said first detector cell is at a maximum when the x-ray source focal spot is aligned with said first x-ray beam passage and the signal output by said second detector cell is at a maximum when the x-ray source focal spot is aligned with said second x-ray beam passage.

15. Apparatus in accordance with claim 12 wherein said attenuator comprises a plurality of spaced, adjacent rectangular blocks, said blocks constructed from x-ray absorbing material and slots are established between adjacent blocks to form said x-ray beam passages.

16. Apparatus in accordance with claim 12 wherein said attenuator comprises a block having cylindrical openings extending therethrough, said cylindrical openings forming said x-ray beam passages.

* * * * *